United States Patent [19]

Renfroe

[11] Patent Number: 4,622,322
[45] Date of Patent: Nov. 11, 1986

[54] AROYL SUBSTITUTED DIHYDRO-1,4-THIAZINES

[75] Inventor: Harris B. Renfroe, West Nyack, N.Y.

[73] Assignee: Ciba-Geigy Corporation, Ardsley, N.Y.

[21] Appl. No.: 625,946

[22] Filed: Jun. 29, 1984

[51] Int. Cl.[4] .................... C07D 279/10; A61K 31/54
[52] U.S. Cl. .................... 514/222; 544/58.2; 544/58.4
[58] Field of Search ............ 544/58.2, 58.4; 514/222

[56] References Cited

U.S. PATENT DOCUMENTS

| 3,452,001 | 6/1969 | Alt et al. | 260/239 |
| 3,835,149 | 9/1974 | Renfroe | 260/297 R |
| 4,427,676 | 1/1984 | White et al. | 424/246 |
| 4,539,320 | 9/1985 | Lang et al. | 514/222 |

FOREIGN PATENT DOCUMENTS 2089796 6/1982 United Kingdom .

OTHER PUBLICATIONS

Hojo et al, 4–Alkyl–2H–1,4–Thiazin–3–Ones Synthesis 1982, 312–312.
Satzinger, Liebigs Ann. Chem. 1978, 473 (e.g. p. 488).
Alexander et al, J. Chem. Soc. Perkin Trans. I, 1974, 2092, 3,4–Dihydro–2H–1,4–Thiazines.
Renfroe, et al, Abstracts of 16th National Medicinal Chemistry Symposium, 1978 pp. 127–132.
Mikaiyama et al, Tetrahedron Letters, 1967, 3439.
Derwent Abstract 95085/E45 of French Patent No. 2509 303 (1/14/83).

Primary Examiner—John M. Ford
Attorney, Agent, or Firm—Norbert Gruenfeld

[57] ABSTRACT

Compounds of the formula

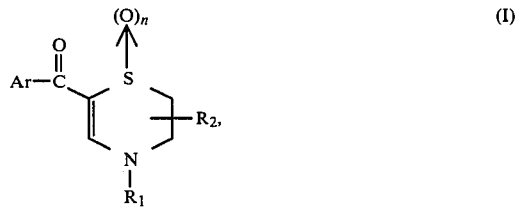

wherein Ar is pyridyl or phenyl substituted by halogen, halo-$C_1$-$C_4$-alkyl, $C_1$-$C_4$-alkoxy, or carboxy-$C_1$-$C_4$-alkyl, n is zero, one or two, $R_1$ is hydrogen, $C_1$-$C_4$-alkyl, heterocyclyl-$C_2$-$C_4$-alkyl, amino-$C_2$-$C_4$-alkyl, $C_1$-$C_4$-alkylamino-$C_2$-$C_4$-alkyl, di-$C_1$-$C_4$-alkylamino-$C_2$-$C_4$-alkyl or $C_1$-$C_4$-alkanoyl, and $R_2$ is hydrogen, carboxy-$C_1$-$C_4$-alkyl, or $C_1$-$C_4$-alkoxy-carbonyl-$C_1$-$C_4$-alkyl are disclosed as well as their preparation, pharmaceutical compositions containing the same and the use thereof as antirheumatic agents.

7 Claims, No Drawings

AROYL SUBSTITUTED DIHYDRO-1,4-THIAZINES

The invention relates to novel compounds of the formula I which are useful as antirheumatic agents, pharmaceutical compositions containing the same, to the use of these compounds as medicaments, for example in a method for treating rheumatic diseases, for example rheumatoid arthritis, by administration of an effective amount of said compounds or compositions to mammals including man, and to processes for preparing these compounds, to intermediates and to processes for preparing these intermediates.

Particularly, the invention relates to a compound of the formula:

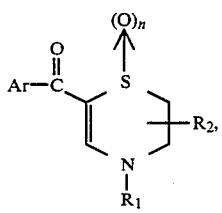

wherein Ar is pyridyl or phenyl substituted by halogen, halo-$C_1$–$C_4$-alkyl, $C_1$–$C_4$-alkoxy, or carboxy-$C_1$–$C_4$-alkyl, n is zero, one or two, $R_1$ is hydrogen, $C_1$–$C_4$-alkyl, heterocyclyl-$C_2$–$C_4$-alkyl, amino-$C_2$–$C_4$-alkyl, $C_1$–$C_4$-alkylamino-$C_2$–$C_4$-alkyl, di-$C_1$–$C_4$-alkylamino-$C_2$–$C_4$-alkyl, or $C_1$–$C_4$-alkanoyl, and $R_2$ is hydrogen, carboxy-$C_1$–$C_4$-alkyl, or $C_1$–$C_4$-alkoxycarbonyl-$C_1$–$C_4$-alkyl, or wherein Ar is phenyl, n is zero, $R_1$ is $C_1$–$C_4$-alkyl, heterocyclyl-$C_2$–$C_4$-alkyl, amino-$C_2$–$C_4$-alkyl, $C_1$–$C_4$-alkylamino-$C_2$–$C_4$-alkyl, di-$C_1$–$C_4$-alkylamino-$C_2$–$C_4$-alkyl or $C_1$–$C_4$-alkanoyl, and $R_2$ is hydrogen, carboxy-$C_1$–$C_4$-alkyl, or $C_1$–$C_4$-alkoxycarbonyl-$C_1$–$C_4$-alkyl, or wherein Ar is phenyl, n is zero, $R_1$ is hydrogen, and $R_2$ is carboxy-$C_1$–$C_4$-alkyl or $C_1$–$C_4$-alkoxycarbonyl-$C_1$–$C_4$-alkyl, or wherein Ar is phenyl, n is one or two, $R_1$ is hydrogen, $C_1$–$C_4$-alkyl, heterocyclyl-$C_2$–$C_4$-alkyl, amino-$C_2$–$C_4$-alkyl, $C_1$–$C_4$-alkylamino-$C_2$–$C_4$-alkyl; di-$C_1$–$C_4$-alkylamino-$C_2$–$C_4$-alkyl or $C_1$–$C_4$-alkanoyl, and $R_2$ is hydrogen, carboxy-$C_1$–$C_4$-alkyl, or $C_1$–$C_4$-alkoxycarbonyl-$C_1$–$C_4$-alkyl, and salts of this compound that has a salt forming group, to a pharmaceutical composition that contains this compound, to the use of this compound as medicament, and to the manufacture of a pharmaceutical composition, and to processes for the manufacture of this compound.

The invention also relates to a pharmaceutical composition that contains a compound of the formula I, wherein Ar is phenyl, n is zero, and $R_1$ and $R_2$ are hydrogen, and a pharmaceutically acceptable salt of this compound, to the use of this compound as medicament, and to the manufacture of a pharmaceutical composition.

In the specification of the present invention, the term "lower", which is used in connection with groups or radicals, for example lower alkyl, lower alkylene, lower alkoxy, lower alkanoyl etc., means that, unless expressly defined otherwise, the groups or radicals so designated contain up to and including 7, and preferably up to and including 4, carbon atoms.

In the compounds of the formula I, n represents especially O. If n represents 1 and $R_2$ is hydrogen, the compounds of formula I exist as enantiomers. If n represents 1 and $R_2$ is other than hydrogen, the compounds of formula I also exist as cis/trans-isomers. Stereoisomers as well as cis/trans-isomers of compounds of the formula I also fall within the scope of the present invention.

The generic terms used in the specification of the invention preferably are defined as follows:

Ar defined as "pyridyl" is, for example, 2-, 3- or 4-pyridyl.

Halogen is for example, bromo or iodo or, preferably, chloro or fluoro.

Halo-$C_1$–$C_4$-alkyl is, for example, fluoromethyl, 2,2,2-trichloroethyl or, preferably, trifluoromethyl.

$C_1$–$C_4$-Alkoxy is, for example, ethoxy or, preferably, methoxy.

Carboxy-$C_1$–$C_4$-alkyl is, for example, 2-carboxyethyl or, preferably, carboxymethyl.

Ar defined as phenyl substituted by halogen, halo-$C_1$–$C_4$-alkyl, $C_1$–$C_4$-alkoxy, or carboxy-$C_1$–$C_4$-alkyl is, for example, 2-fluoro-, 2-chloro-, 2-, 3- or 4-trifluoromethyl-, 2- or 3-methoxy- or 2-, 3- or 4-carboxymethylphenyl, or, preferably, 3- or 4-fluoro-, 3- or 4-chloro-, 3,4-dichloro-, or 4-methoxyphenyl.

$C_1$–$C_4$-Alkyl $R_1$ is for example, ethyl, n-propyl, isopropyl, n-butyl, tert-butyl, sec-butyl or, preferably, methyl.

Heterocyclyl-$C_2$–$C_4$-alkyl $R_1$ is, for example, 2-(piperazin-1-yl)-ethyl, 2-(1-methylpiperazin-4-yl)-ethyl, 2-(1-(2-hydroxyethyl)-piperazin-4-yl)-ethyl, 2-(morpholin-1-yl)-ethyl, or, preferably, 2-(piperid-1-yl)-ethyl.

Amino-$C_2$–$C_4$-alkyl $R_1$ is, for example, 3-amino-n-propyl or, preferably, 2-aminoethyl.

$C_1$–$C_4$-Alkylamino-$C_2$–$C_4$-alkyl $R_1$ is, for example, 3-methylamino-n-propyl or, preferably, 2-methylaminoethyl.

Di-$C_1$–$C_4$-alkylamino-$C_2$–$C_4$-alkyl $R_1$ is, for example, 3-dimethylamino-n-propyl or, preferably, 2-dimethylaminoethyl.

$C_1$–$C_4$-Alkanoyl $R_1$ is, for example, formyl or propionyl or, preferably, acetyl.

Carboxy-$C_1$–$C_4$-alkyl $R_2$ is, for example, 2-carboxyethyl or, preferably, carboxymethyl.

$C_1$–$C_4$-Alkoxycarbonyl-$C_1$–$C_4$-alkyl $R_2$ is, for example, 2-methoxy- or 2-ethoxycarbonylmethyl or, preferably, 2-methoxy- or 2-ethoxycarbonylethyl.

Salts of compounds of the formula I which contain a salt forming group are, in particular, pharmaceutically acceptable non-toxic salts.

Such salts are formed by the carboxy group, when Ar is phenyl substituted by carboxy-$C_1$–$C_4$-alkyl or $R_2$ is carboxy-$C_1$–$C_4$-alkyl by addition of a base and are, for example, metal or ammonium salts, for example alkali metal or alkaline earth metal salts, for example sodium, potassium, magnesium or calcium salts, or ammonium salts, which are formed by addition of ammonia or a suitable organic amine, for example, 2-triethylamine, choline, morpholine, piperazine, piperidine, dicyclohexylamine, pyridine, collidine, or quinoline.

Salts are also formed when $R_1$ represents amino-$C_2$–$C_4$-alkyl, $C_1$–$C_4$-alkylamino-$C_2$–$C_4$-alkyl, di-$C_1$–$C_4$-alkylamino-$C_2$–$C_4$-alkyl or heterocyclyl-$C_2$–$C_4$-alkyl, by additon of an inorganic acid, for example hydrochloric acid, sulfuric acid, or phosphoric acid, and are, for example, hydrochlorides, hydrogensulfates, hydrogenphosphates, or dihydrogenphosphates.

The functional groups present in compounds of the formula I, for example the carboxy group, when Ar is phenyl substituted by carboxy-$C_1$–$C_4$-alkyl or $R_2$ is carboxy-$C_1$-$C_4$-alkyl, or the secondary amino group, when $R_1$ is hydrogen, are optionally protected by protecting groups which are customarily used in peptide chemistry. These protecting groups protect the functional groups from undesired side reactions, such as acylation, etherification, esterification, oxidation, solvolysis etc. and are removed easily under mild reaction conditions, for example by solvolysis, reduction, photolysis, or enzymatic cleavage.

The protection of functional groups by such protecting groups, the protecting groups themselves, and reactions for their removal, are described, for example, in "Protective Groups in Organic Chemistry", Plenum Press, London and New York 1973, in Greene, Th. W., "Protective Groups in Organic Synthesis", Wiley, N.Y. 1981, in "The Peptides", Vol. I, Schroeder and Luebke, Academic Press, London and New York 1965, and in "Methoden der Organischen Chemie", Houben-Weyl, 4th Edition, Vol. 15/I, Georg Thieme Verlag, Stuttgart 1974.

A protected carboxy group is preferably tert-lower alkoxycarbonyl, for example tert-butoxycarbonyl, benzyloxycarbonyl, 4-nitrobenzyloxycarbonyl or diphenylmethoxycarbonyl.

When a carboxy group is present, this group can also be protected by a group that can be cleaved under physiological conditions, for example enzymatically. Such groups are, for example, lower alkanoyloxy-lower alkoxycarbonyl, for example lower alkanoyloxymethoxycarbonyl or lower alkanoyloxyethoxycarbonyl, for example acetoxymethoxycarbonyl, pivaloyloxymethoxycarbonyl or 1-propionyloxyethoxycarbonyl, lower alkoxycarbonyloxy-lower alkoxycarbonyl, for example 1-ethoxycarbonyloxyethoxycarbonyl or tert-butoxycarbonyloxymethoxycarbonyl, or amino-lower alkanoyloxymethoxycarbonyl, for example glycyloxymethoxycarbonyl, L-valyloxymethoxycarbonyl, or L-leucyloxymethoxycarbonyl.

A protected amino group is preferably tert-butoxycarbonylamino (BOC), 4-nitrobenzyloxycarbonylamino, diphenylmethoxycarbonylamino, or 2,2,2-trichloroethoxycarbonylamino.

In an alphabetically increasing order of preference, the invention relates to the following compounds of the formula I:

(a) Compounds of the formula I, wherein Ar is pyridyl or phenyl substituted by halogen, for example fluoro or chloro, trifluoromethyl, $C_1$-$C_4$-alkoxy, for example methoxy, or carboxy-$C_1$-$C_4$-alkyl, for example, carboxymethyl, n is zero, one or two, $R_1$ is hydrogen, $C_1$-$C_4$-alkyl, for example methyl, heterocyclyl-$C_2$-$C_4$-alkyl, for example 2-(piperid-1-yl)-ethyl, di-$C_1$-$C_4$-alkylamino-$C_2$-$C_4$-alkyl, for example 2-dimethylaminoethyl, or $C_1$-$C_4$-alkanoyl, for example acetyl, and $R_2$ is hydrogen or carboxy-$C_1$-$C_4$-alkyl, for example carboxymethyl, and pharmaceutically acceptable salts of those compounds that have salt forming groups;

(b) Compounds of the formula

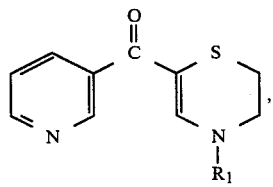

(Ia)

wherein $R_1$ represents hydrogen, $C_1$-$C_4$-alkanoyl, for example acetyl, or $C_1$-$C_4$-alkyl, for example methyl, or compounds of the formula

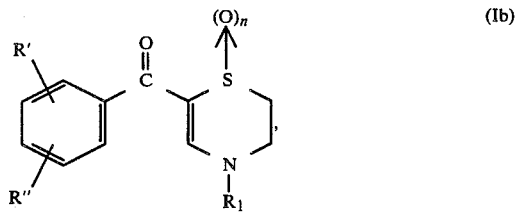

(Ib)

wherein $R_1$ is as defined under formula Ia, n is zero, one, or two, R' is hydrogen, trifluoromethyl, or halogen, for example fluoro or chloro, and R" is halogen, for example fluoro or chloro, and pharmaceutically acceptable salts of those compounds that have salt forming groups;

(c) Compounds of the formula Ib, wherein $R_1$ is hydrogen, n is zero, R' is hydrogen, trifluoromethyl, or halogen, for example fluoro or chloro, and R" is halogen, for example fluoro or chloro.

(d) A compound of the formula Ib, wherein $R_1$ is hydrogen, n is zero, R' is hydrogen and R" is 4-fluoro being 5,6-dihydro-1,4(4H)-thiazin-2-yl 4-fluorophenyl ketone.

The compounds of the invention and the compound of the formula I, wherein Ar is phenyl, n is zero, and $R_1$ and $R_2$ are hydrogen, exhibit valuable pharmacological properties, especially antirheumatic activity. These properties can be demonstrated by in-vitro or in-vivo tests, using for the latter advantageously mammals, such as mice, rats, guinea pigs or dogs, as test objects. The compounds according to the present invention can be administered to the animals either enterally, preferably orally, parenterally, e.g. subcutaneously or intravenously, or topically, for example in the form of oil solutions or starchy suspensions. The applied dosage may range between 0.1 and 100 mg/kg per day, preferably between about 1 and 50 mg/kg per day. The tests for the screening are chosen from the following assay methods:

1. Developing Adjuvant Arthritis Test

Charles River (COBS-CD) male rats weighing 325–400 g are injected with 0.05 ml of saline/oil emulsion of *Mycobacterium tuberculosis* (Difco, 6 mg/ml) into the subplantar region of the right hind paw (day 1). On day 3 after injection, animals showing a good inflammatory response are selected and assigned to treatment groups of nine rats each with three rats per cage. The test compound is suspended in an aqueous cornstarch vehicle [3% (w/v) cornstarch, 5% (w/v)polyethylene glycol 400 and 0.34% (w/v) Tween 80] by grinding and mixing with a ground glass homogenizer. Vehicle, and test compound are administered orally (10 ml/kg) once daily for 12 days beginning on the third day after adjuvant injection.

Left hind paws are measured by mercury displacement on day 15. Mercury displacement for each group on day 15 is expressed as mean displacement (M). Significance is determined by comparing treated means (MTR) with adjuvant control mean (MAC). Body weights are reported as differences between day 3 and day 15. The percent protection(%P) is caluated on swelling (Mean displacement of paws corrected for normal control):

$$\% P = \frac{MAL - MTR}{MAL - MNC} \times 100$$

(MAC = Mean Adjuvant Control Day 15,

MTR=Mean Treated Day 15, Mean Normal Control Day 15)). Experiments are run at 12.5, 25, and 50 mg/kg p.o. with 5,6-dihydro-1,4(4H)-thiazin-2-yl 4-fluorophenyl ketone as representative test compound and replicated. All treatments are effective in suppressing paw volume as compared to the development of this polyarthritis in adjuvant treated controls. At 12.5 mg/kg p.o. 55.8% protection is observed, at 25.0 mg/kg 49.0% and at 50.0 mg/kg 67.7%.

2. Carrageenan-Induced Pleurisy Test

Sprague Dawley male rats (Charles River) weighing 300–325 g are used. Pleurisy is induced by injecting 0.3 ml of 1% sterile, aqueous solution of carrageenan into the pleural cavity of the rats. Carrageenan is solubilized in distilled water by autoclaving. Seventy-two hours after the carrageenan injection, the inflammatory exudate cells are collected with a Pasteur pipette by washing the cavity with 4 ml of medium 199 containing 5 units heparin per ml. Heparin is used to prevent cell aggregation. Any animals with blood in the pleural cavity are rejected. Total leukocyte counts are performed with a Coulter counter, Model $ZB_1$, using a 20 microliter aliquot of pleural exudate in 10 ml of Isotone ®. Differential counts of exudate smears are determined by standard procedures.

The rats are distributed into treatment groups of 10–12 with two or three rats per cage. Each rat receives a marking on the tail for proper identification. The test compound is suspended in an aqueous cornstarch vehicle by grinding and mixing with a ground glass homogenizer. Vehicle and the test compound are administered orally in a volume of 10 ml/kg once daily for 3 days beginning 1 hour prior to intrapleural injection of carrageenan. Twenty-four hours after the last dose the rats are sacrificed and their pleural cells collected and counted. Differential counts are made as needed.

In this assay, the percent of reduction in cellular infiltration into the pleural cavity of the treated rats compared to controls is determined and checked for statistical significance using Student's t-test. Statistical analysis of the data, using cellcounts rather than percent change, is performed by using the Brown-Forsythe method.

The experiments are run with 5,6-dihydro-1,4(4H)-thiazin-2-yl 4-fluorophenyl ketone as representative test compound with 11 rats per group at a dose of 25 mg/kg p.o. and 12 rats per group at a dose of 50 mg/kg. Results: Control (12 animals): 143.9±11.9 (cell count×$10^6$), test compound: 115.8±12.8 at a dose of 25 mg/kg, 71.1±5.0 at a dose of 50 mg/kg (cell count×$10^6$).

The compounds of this invention are also active in the decrease of neutrophil adherence assay described in Amer. J. Med. 61, 597 (1976).

The advantageous pharmacological properties render the compounds of the present invention useful as disease-modifying antirheumatic agents especially for the treatment and amelioration of e.g. rheumatic disorders, such as rheumatoid arthritis in mammals, including man.

The pharmaceutical compositions according to the invention are those suitable for enteral, such as oral or rectal, parenteral such as subcutaneous or intraveneous, or topical administration to mammals, including man, for the treatment of rheumatic diseases such as rheumatoid arthritis comprising an effective amount of a pharmacologically active compound of formula I, or a pharmaceutically acceptable salt thereof, exclusively or in combination with one or more pharmaceutically acceptable adjuvants or carriers.

The pharmacologically active compounds of the invention are useful in the manufacture of pharmaceutical compositions containing an effective amount thereof in conjunction or admixture with excipients suitable for either enteral, parental or topical application. Preferred are tablets and gelatin capsules comprising the active ingredient together with (a) diluents, e.g. lactose, dextrose, sucrose, mannitol, sorbitol, cellulose and/or glycine; (b) lubricants, e.g. silica, talcum, stearic acid, its magnesium or calcium salt and/or polyethyleneglycol; for tablets also (c) binders, e.g. magnesium aluminum silicate, starch paste, gelatine, traganth, methylcellulose, sodium carboxymethylcellulose and/or polyvinylpyrrolidone; if desired, (d) disintegrants, e.g. starches, agar, alginic acid or its sodium salt, or effervescent mixtures; and/or (e) absorbents, colorants, flavors and sweeteners. Injectable compositions are preferably aqueous isotonic solutions or suspensions and suppositories. Topical lotions are advantageously made from fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compostions may also contain other therapeutically valuable substances. They are prepared according to conventional mixing, granulating or coating methods respectively and contain about 0.1 to 75%, preferably about 1 to 50%, of the active ingredient.

A unit dosage for a mammal of about 50 to 70 kg may contain between about 10 to 200 mg of the active ingredient.

The compounds of formula I, wherein $R_1$ is hydrogen, are prepared by the following processes, preferably by (a) cyclizing a compound of the formula

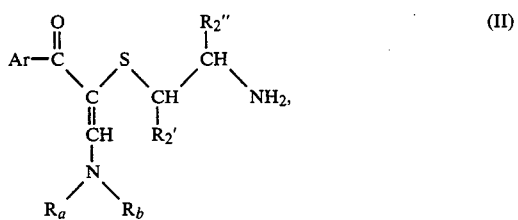

wherein Ar is defined as above, $R_a$ and $R_b$ are $C_1$–$C_4$-alkyl, $R_2'$ and $R_2''$ are hydrogen or one of $R_2'$ and $R_2''$ is hydrogen and the other is carboxy-$C_1$–$C_4$-alkyl or $C_1$–$C_4$-alkoxycarbonyl-$C_1$–$C_4$-alkyl, and wherein the amino group is in the free form or is protected by a conventional amino protecting group, in the presence of a base or (b) condensing a compound of the formula

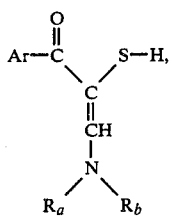

(III)

wherein Ar and $R_a$ and $R_b$ are defined as above and wherein the mercapto group is in the free form or is protected by a conventional mercapto protecting group with a compound of the formula

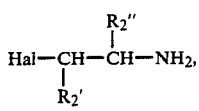

(IV)

wherein Hal is chloro, bromo or iodo and $R_2'$ and $R_2''$ are defined as above, or with an acid addition salt thereof in the presence of base and, if desired, converting a resulting compound into another compound of the invention and/or converting a resulting salt into the free compound or into a different salt and/or converting, a resulting free compound having a salt forming group into a salt.

Process (a)

In a compound of the formula II, $R_a$ and $R_b$ are especially methyl, and $R_2'$ and $R_2''$ are especially hydrogen.

The protection of the amino group by a conventional protecting group is described in the references mentioned above with respect to the protection of the carboxy group.

The amino group can, for example, be protected in the form of an acylamino or, preferably, in the form of an acylimido group.

In an acylamino group, acyl is, for example, the acyl group of an organic carboxylic acid having up to 10 carbon atoms, especially of an unsubstituted lower alkanecarboxylic acid, or of a lower alkanecarboxylic acid that is substituted, for example, by halogen or aryl, or of a benzoic acid that is unsubstituted or substituted, for example, by halogen, lower alkoxy or nitro, or of a carbonic acid semi-ester. Such an acyl group is, for example, 2,2,2-trifluoro- or 2,2,2-trichloroacetyl, benzoyl, or benzoyl substituted, for example, by halogen, for example chlorine, lower alkoxy, for example methoxy, or by nitro, for example benzoyl, 4-chlorobenzoyl, 4-methoxybenzoyl, or 4-nitrobenzoyl, or lower alkoxycarbonyl that is branched in the 1-position of the lower alkyl radical or is substituted in the 1- or 2-position by suitable substitutents.

Lower alkoxycarbonyl branched in the 1-position of the lower alkyl radical is, for example, tert-lower alkoxycarbonyl, for example tert-butoxycarbonyl (BOC), arylmethoxycarbonyl having one or two aryl radicals wherein aryl is preferably phenyl that is unsubstituted or mono-, di- or tri-substituted, for example, by lower alkyl, especially tert-lower alkyl, for example tert-butyl, lower alkoxy, for example methoxy, hydroxy, halogen, for example chlorine, and/or by nitro, for example diphenylmethoxycarbonyl or di-(4-methoxyphenyl)methoxycarbonyl.

Lower alkoxycarbonyl substituted in the 1- or 2-position by suitable substituents is, for example, aroylmethoxycarbonyl, for example phenacyloxycarbonyl, 2-halo-alkoxycarbonyl, for example 2,2,2-trichloroethoxycarbonyl, 2-bromoethoxycarbonyl or 2-iodoethoxycarbonyl, or 2-(tri-substituted silyl)-ethoxycarbonyl in which the silyl group is substituted by organic radicals, for example lower alkyl, phenyl-lower alkyl or phenyl, for example 2-tri-lower alkylsilylethoxycarbonyl, for example 2-trimethylsilylethoxycarbonyl or 2-(di-n-butyl-methylsilyl)ethoxycarbonyl, or 2-triphenylsilylethoxycarbonyl.

In an acylimido group acyl is preferably the acyl group of a dicarboxylic acid, for example succinic, glutaric or phthalic acid.

The amino group preferably is protected in the form of a succinimido or phthalimido group.

A suitable base is a primary amine, preferably a lower alkylamine, for example n-butylamine, or a secondary amine, for example a di-lower alkylamine, for example diisopropylamine.

The cyclisation is generally carried out in organic inert solvents, such as suitable alcohols, such as methanol, ethanol or isopropanol, ketones, such as acetone, ethers, such as dioxan or tetyrahydrofuran, nitriles, such as acetonitrile, halogenated hydrocarbons, such as methylene chloride, chloroform or carbon tetrachloride, esters, such as ethyl acetate, or amides, such as dimethylformamide or dimethylacetamide, and the like. The reaction temperature is between room temperature and the boiling temperature of the reaction mixture, preferably between 60° C. and the boiling temperature of the reaction mixture.

The cyclisation is preferably carried out under inert gas atmosphere, preferably nitrogen atmosphere.

Process (b)

In a compound of formula III, $R_a$ and $R_b$ are especially methyl.

The protection of the mercapto group by a conventional protecting group is described in the references mentioned above with respect to the protection of the carboxy group.

The mercapto group can, for example, be protected in the form of an acylthio group.

In an acylthio group acyl is, for example halosubstituted lower alkanoyl, for example 2,2-dichloroacetyl, or, especially, the acyl radical of a carbonic acid semiester mentioned above in connection with protected amino groups, for example, 2,2,2-trichloroethoxycarbonyl, or 4-nitrobenzyloxycarbonyl, or, preferably, lower alkanoyl, for example formyl or acetyl.

The mercapto group preferably is protected by the formyl or acetyl group.

A suitable base is an inorganic base, for example an alkali metal or alkaline earth metal hydroxide, carbonate or bicarbonate, for example sodium, potassium or calcium hydroxide, carbonate or bicarbonate, or preferably an alkali metal alcoholate, for example sodium or potassium methylate, ethylate or tert-butylate.

The condensation of a compound of the formula III with a compound of the formula IV is preferably carried out in an inert, preferably anhydrous, solvent or solvent mixture, for example in a carboxylic acid amide, for example a formamide, for example dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in mixtures thereof, preferably in an alcohol, for example methanol or ethanol, or water, optionally at reduced or elevated temperature, for example in a temperature range from approximately −40° C. to approximately +100° C., preferably from approximately −10° C. to room temperature, and optionally under an inert gas atmosphere, for example nitrogen atmosphere.

The compounds of the invention, so obtained, can be converted into each other according to methods known per se. For example, if $R_1$ is hydrogen, the secondary amino group can be acylated to give compounds wherein $R_1$ is $C_1$–$C_4$-alkanoyl. The acylation can be effected by reaction with a suitable acylating agent which introduces the $C_1$–$C_4$-alkanoyl radical, for example formic or acetic acid, or a reactive, functional derivative thereof.

A reactive, functional derivative of a carboxylic acid is an anhydride of this carboxylic acid or a mixed anhydride. A mixed anhydride is formed e.g. by condensation with another acid, e.g. an inorganic acid such as a hydrohalic acid, and is, for example, the corresponding carboxylic acid halide, e.g. the carboxylic acid chloride or bromide. A reactive functional derivative of a carboxylic acid of the formula III is furthermore formed by condensation with a lower alkyl hemiester of carbonic acid, e.g. the ethyl or isobutyl hemiester of carbonic acid.

The acylation reactions are preferably carried out in the presence of a suitable acid acceptor, for example of a suitable organic base. A suitable organic base is e.g. an amine, e.g. a tertiary amine such as a tri-lower alkylamine, e.g. trimethylamine or triethylamine, a cyclic tertiary amine such as N-methylmorpholine, a bicyclic amidine, e.g. a diazabicycloalkene such as 1,5-diazabicyclo[4.3.0]non-5-ene or 1,5-diazabicyclo[5.4.-0]undec-5-ene (DBU), or is, for example, a base of the pyridine type, e.g. pyridine. A suitable acid acceptor is also an inorganic base, for example an alkali metal hydroxide or alkaline earth metal hydroxide, e.g. sodium, potassium or calcium hydroxide.

The acylation reactions are preferably carried out in an inert, preferably anhydrous, solvent or mixture of solvents, for example in dimethylformamide, methylene chloride, carbon tetrachloride, chlorobenzene, acetone, tetrahydrofuran, ethyl acetate or acetonitrile, or in mixtures thereof, if desired at low or elevated temperature, e.g. in the temperature range from about −40° C. to +100° C., preferably from about −10° C. to +50° C., and optionally in an inert gas atomsphere, e.g. under nitrogen.

If in a compound of formula I $R_1$ is hydrogen, the secondary amino group can be alkylated with a suitable alkylating agent that introduces the $C_1$–$C_4$-alkyl- or the heterocyclyl-$C_2$–$C_4$-alkyl group to give compounds of the formula I, wherein $R_1$ is $C_1$–$C_4$-alkyl or heterocyclyl-$C_2$–$C_4$-alkyl. The secondary amino group is treated with a suitable metallating agent, for example sodium or lithium diisopropylamide, butyllithium or potassium hydride, and the metallated compound is reacted with an alkylating reagent, for example methyliodide or 2-(piperid-1-yl)-ethylchloride.

If in a compound of the formula I $R_2$ is carboxy-$C_1$–$C_4$-alkyl, the free carboxy group can be converted into a carboxy group that can be cleaved under physiological conditions, for example enzymatically, by esterification methods known per se.

For example, a compound of the formula I in which the carboxy group to be esterified is in the free form or a compound of the formula I in which the carboxy group to be esterified is in the form of a reactive, functional derivative, for example in the form of an acid chloride, or a salt of a compound of the formula I is reacted with the corresponding alcohol or with a reactive functional derivative of this alcohol, for example the halide, e.g. chloride.

If in a compound of the formula I $R_2$ is $C_1$–$C_4$-alkoxycarbonyl-$C_1$–$C_4$-alkyl, the ester can be converted to the free carboxylic acid of formula I, wherein $R_2$ is carboxy-$C_1$–$C_4$-alkyl, for example by known ester cleavage methods, for example saponification under acid conditions, for example by reaction with hydrochloric acid or sulfuric acid, or by reaction with sodium or potassium hydroxide and converting the salt obtained to the free acid.

A compound of the formula I wherein n is zero, can be converted to a compound of the formula I wherein n is one, by adding one equivalent of an oxidizing agent. Such oxidizing agents are especially hydrogen peroxide or organic peracids, especially aliphatic percarboxylic acids, for example peracetic acid, perbenzoic acid, m-chloroperbenzoic acid, or monoperphthalic acid.

A compound of the formula I wherein n is zero or one, can be converted to a compound of the formula I wherein n is two, by reaction with two equivalents or an excess or one equivalent of the oxidizing agents mentioned above.

The oxidation is preferably carried out in a suitable non-aqueous inert solvent, for example a halogenated hydrocarbon, for example methylene chloride, chloroform or carbon tetrachloride, an alcohol, for example methanol or ethanol, a ketone, for example acetone, an amide, for example dimethylformamide, or a liquid organic carboxylic acid, for example acetic acid, or in a mixture of these solvents, at room temperature, or while cooling or gently heating, for example from approximately −50° C. to approximately +40° C., preferably from approximately −20° C. to approximately 0° C. The oxidation can also be carried out in stages by first oxidizing at low temperature, that is to say from approximately −20° C. to approximately −10° C., to the sulfoxide stage (n=1), which is optionally isolated, and then in a second stage, by oxidizing the sulfoxide to the sulfone (n=2), preferably at higher temperature, for example from −10° C. to 0°.

For working up, excess oxidizing agent which may still be present can be eliminated by reaction with a reducing agent, for example a thiosulfate, for example sodium thiosulfate.

A 1-oxide of the formula I in which n is 1, and a 1,1-dioxide in which n is 2, can be converted by various reducing agents, for example phosphorous trichloride, into the corresponding 1-sulfide in which n is 0.

Salts of compounds of the formula I can be manufactured in a manner known per se. Thus, salts of compounds of the formula I can be prepared by reaction of a compound having a carboxy group with aqueous solutions of alkaline metal hydroxides, such as sodium or potassium hydroxide or with ammonia or a suitable organic amine, preferably stoichiometric quantities or only a small excess of the salt-forming agent being used. Acid addition salts of compounds of the formula I wherein $R_1$ is hydrogen are obtained in the customary manner, for example by treatment with an acid or a suitable anion exchange reagent. Salts can be converted into the free compounds in customary manner; metal and ammonium salts can be converted, for example, by treatment with suitable acids, and acid addition salts can be converted, for example, by treatment with a suitable basic agent.

The invention also includes those partial embodiments according to which compounds formed as intermediates are used as starting materials and the remaining process steps are carried out with these, or the process is discontinued at any stage; furthermore, starting materials may be used in the form of derivatives or may be formed during the reaction.

Preferably, the starting materials and the reaction conditions are so chosen that the compounds described above as being especially preferred are obtained.

The starting materials employed in the process for the preparation of compounds of the formula I are known or, if they are novel, can be obtained in a manner known per se.

Starting materials of the formula II are novel and are also subject matter of the present invention. They can be prepared by reacting a compound of the formula:

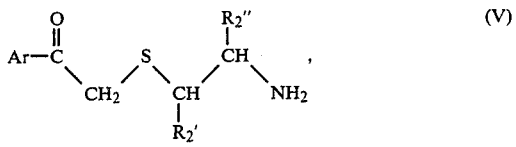

wherein Ar, $R^{2'}$ and $R^{2''}$ are defined as above and wherein the amino group is protected by a conventional amino protecting group, with a reactive, functional derivative of N,N-di-$C_1$-$C_4$-alkylformamide. A conventional amino protecting group is mentioned above under Process (a) and is, preferably, phthaloyl. A reactive, functional derivative of N,N-di-$C_1$-$C_4$-alkylformamide, for example dimethylformamide, is, for example, a formininium salt of the formula

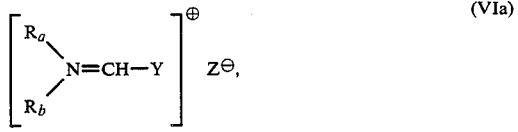

wherein $R_a$ and $R_b$ are lower alkyl, for example ethyl, preferably methyl, Y is halogen, for example bromine, or, preferably, chlorine, lower alkoxy, for example ethoxy, or, preferably, methoxy, or benzyloxy, and Z is halogen, preferably chlorine, lower alkoxy, the radical of an alkylating agent, for example monomethylsulfate, orthodimethylphosphate, or the tetrafluoroborate radical, or is a formamide acetal of the formula

wherein $R_a$ and $R_b$ are defined as above and alk is methyl or ethyl.

The formiminium salt of the formula VIa, wherein Y and Z are halogen, can be obtained by reacting a N,N-di-$C_1$-$C_4$-alkylformamide, for example dimethylformamide with a halogenating agent, for example oxalyl chloride, phosgene, diphosgene (trichloromethyl chloroformate), phosphoryl chloride, phosphorous pentachloride or thionyl chloride. Compounds of the formula VIa, wherein Y is lower alkoxy, preferably methoxy, and Z is the radical of an alkylating agent, for example the monomethylsulfate radical or the tetrafluoroborate radical, are obtained by reacting the N,N-di-$C_1$-$C_4$-alkylformamide with an alkylating agent, for example a lower alkyl halide, for example methyl iodide, or a lower alkylsulfate, for example dimethylsulfate, or by reaction with a tri-lower alkyloxonium salt, for example trimethyloxoniumtetrafluoroborate. These reactions are carried out in an inert, dry solvent, especially in methylene chloride, chloroform, diethylether, benzene or toluene at temperatures between about $-10°$ and the boiling point of the reaction mixture. The resulting formiminium salt can be isolated and purified or, as described above, produced and used further in situ.

The formamide acetal of the formula VIb can be obtained by reacting an alcohol, such as a lower alkanol, for example methanol or ethanol, with an iminium ether salt of the formula IIa described above (Y=lower alkoxy or benzyloxy), preferably in the presence of basic agents, for example alcoholates, for example sodium methylate, or by treating a dialkylamine, for example dimethylamine, with an activated or reactive derivative of orthoformic acid such as an ester or an amide acetal thereof, for example with an orthoester of formic acid, preferably in the presence of Lewis catalysts, for example with trimethyl orthoformate and $ZnCl_2$ or boron trifluoride etherate or by treating a N,N-di-$C_1$-$C_4$-alkylformamide, for example dimethylformamide, in a manner known per se with an acetalizing agent, such as a trialkyloxonium tetrafluoborate, for example triethyloxonium tetrafluoborate, and, if desired, subsequently treating the reaction product with a basic agent, for example with sodium methylate.

The reaction conditions are known and their choice depends in particular on the vigor of the reaction to be expected. Thus, the reaction of an iminium ether salt with sodium methylate or an alcohol in the presence of a tertiary base is preferably carried out with cooling, for example at temperatures of about $-70°$ C. to about $+10°$ C. However, it is also possible to carry out the reaction at higher temperatures, i.e. for example, of up to about $75°$ C., if the stability of the starting materials and of the reaction products permits a higher temperature.

The process variant which proceeds via the starting materials of the formula VIa is advantageously carried out in an inert organic solvent; the process variant which proceeds via the starting compounds of the formula VIb using orthoformates as the condensing agent preferably proceeds in the presence of an alkylating catalyst, such as a Lewis acid, for example zinc chloride or boron trifluoride etherate.

Suitable inert solvents or diluents are dry, preferably polar, solvents which do not possess any reactive functional groups. In particular, halogenated hydrocarbons, especially methylene chloride or chloroform, and also ketones, such as acetone, ethers, such as diethyl ether, anisole or tetrahydrofuran, and also aromatic hydrocarbons, for example benzene or toluene, or esters which are stable to hydrolysis, such as ethyl acetate, are suitable as solvents.

Compounds of the formula II can also be prepared by reacting a compound of the formula

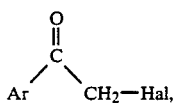

wherein Ar is defined as above and Hal is bromine or iodine, preferably chlorine, with an ethylene episulfide compound of the formula

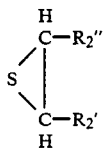

wherein $R_2'$ and $R_2''$ are defined as above, reacting the salt obtained of the formula

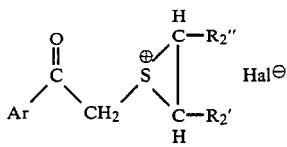

with the formamide acetal of the formula VIb to give a compound of the formula

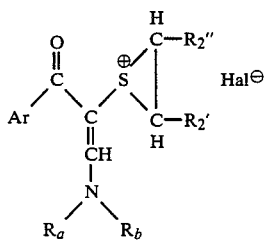

which is reacted with ammonia to give a compound of the formula II.

Starting materials of the formula III are novel and are also subject matter of the present invention. They can be prepared by reacting a compound of the formula

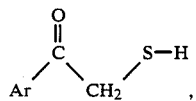

wherein Ar is defined as above and wherein the mercapto group is protected by a conventional mercapto protecting group, with a reactive, functional derivative of N,N-di-$C_1$-$C_4$-alkylformamide.

A conventional mercapto protecting group is mentioned above and is preferably acetyl. A reactive, functional derivative of N,N-di-$C_1$-$C_4$-alkylformamide is, for example, a formimium salt of the formula VIa or a formamide acetal of the formula VIb. The process is carried out in a manner analogous to the process for the preparation of compounds of the formula V.

Starting materials of the formula IV are known. They are commercially available or can be prepared by known methods.

Starting materials of the formula V are novel and are also subject matter of the present invention. They can be prepared by condensing a thioester of the formula

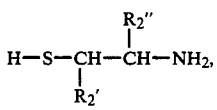

wherein $R_2'$ and $R_2''$ are defined as above and wherein the amino group is protected by a conventional amino protecting group, under intermediary protection of the mercapto group with a conventional mercapto protecting group with a halide of the formula

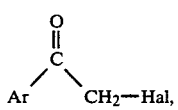

wherein Ar is defined as above and Hal is bromine or iodine, preferably chlorine, in the presence of a base.

A conventional amino protecting group is mentioned above under Process (a) and is, preferably, phthaloyl. A conventional mercapto protecting group is mentioned above and is preferably acetyl. This protecting group is split off during the process. This process can be carried out with the same base, preferably sodium methoxide, in the same solvent, e.g. ethanol, and under the same reaction conditions mentioned above under process (b).

Compounds of formula VIa and VIb are known. Their preparation is described in Houben-Weyl, Methoden der Organischen Chemie, Thieme Verl. Stuttgart 1965, Sauerstoff-Verbindungen I, Teil 3, pg. 199–367, Starting materials of the formula VII are known or, if they are novel, can be prepared by condensing a compound of the formula IX with a compound of the formula $$R_o\text{—S—H} \qquad (X),$$

wherein $R_o$ is a leaving group, preferably acetyl, in the presence of a base.

This process can be carried out with the same base, preferably sodium methoxide, in the same solvent, e.g. ethanol, and under the same reaction conditions mentioned above under process (b).

Compounds of the formulae VII, VIII, IX and X are known and are either commercially available or can be prepared according to known methods.

The following examples are intended to illustrate the invention and are not to be construed as being limitations thereon. Temperatures throughout are given in degrees Centigrade and all parts wherever given are parts by weight. If not otherwise stated, evaporations are carried out under reduced pressure, preferably between about 15 and 100 mm Hg.

IR-spectra in cm$^{-1}$, chemical shifts in the NMR spectra ($\delta$) in ppm; m: multiplett; s: singlett; d: doublett; t: triplett.

EXAMPLES

1. 5,6-Dihydro-1,4(4H)-thiazin-2-yl 4-fluorophenyl ketone 2.527 kg (34.5M) n-Butylamine is added to a stirred solution of 23 l ethanol and 4.58 kg (11,5M) 2-[2-(2-dimethylamino-1-(4-fluorobenzoyl)vinylthio)ethyl]-1,3-isoindoledione under nitrogen atomsphere and the solution is heated at reflux temperature for 24 hours. The reaction mixture is cooled and stirred at 10° for 3 hours. The crude product is collected by filtration, washed several times with ethanol and ether and dried. The crude product is dissolved at 90° in dimethylformamide and the solution is filtered through a heated funnel. A solid begins to form and the resulting suspension is stirred at room temperature overnight, filtered, washed with ether and dried. M.P. 212°–214° ; IR (N): NH 3100, C=O 1580; NMR (DMSO): 7.02–7.55 (m, 6H), 3.48 (m, 2H), 2.77 (m, 2H).

The starting material is prepared as follows:

(a) 2-(Acetylthioethyl)-1,3-isoindoledione 0.855 kg (7.9M) Potassium-tert-butoxide is added in portions at −5° under nitrogen atmosphere to 4 l dimethylformamide. A solution of 0.6 kg (7.9M) thioacetic acid in 2 l dimethylformamide is added in a steady stream at such a rate that the temperature can be maintained between −5° and 0° . The reaction mixture is then stirred for 1 hour at −5° . 2.0 kg (7.9M) N-(2-bromoethyl)phthalimide in 4 l dimethylformamide is added to the reaction mixture at such a rate that the temperature does not exceed 5° and the reaction mixture is stirred for 2 hours. 40 l of water cooled at 5°–10° are added which raises the reaction temperature to 20° . The reaction mixture is stirred overnight at room temperature and filtered. The crude product is washed with water and dried. M.P. 112°–114°.

(b) 2-(2-(4-fluorobenzoylmethylthio)ethyl)-1,3-isoindoledione 0.803 kg (14.8M) sodium methoxide in 16 l of ethanol is added to a stirred solution of 3.7 kg (14.8M) 2-(acetylthioethyl)-1,3-isoindoledione in 29.2 l ethanol at 0° . The temperature is maintained between 0°–5° and the reaction mixture is stirred for one hour. 3.23 kg (14.8M) a-bromo-4-fluoroacetophenone in 14.6 l of ethanol is added at such a rate to maintain the temperature between 0° and 10° . The reaction mixture is stirred overnight at room temperature. The product is collected by filtration, washed with ethanol and ether and dried. M.P. 123.5°–125.5°.

(c) 2-[2-(2-dimethylamino-1-(4-fluorobenzoyl)vinylthio)-ethyl]-1,3-isoindoledione 1.525 kg (12.8M) of dimethylformamide dimethylacetal is added to a solution of 4.4 kg (12.8M) in 44 l dichloromethane. The solution is heated at reflux temperature for 24 hours, another 0.76 kg (6.4M) of the acetal are added and the solution is heated under reflux for another 24 hours. The solvent is removed at reduced temperatures and the heavy oil residue is dissolved in isopropanol at 70° . A solid is formed after stirring overnight which is collected by filtration, washed with ether and dried. M.P. 108°–111° ; IR (N): NH 3200, C=O 1610; NMR (DMSO): 7.47 (s), 7.30 (d), 3.53 (m, 2H), 2.83 (dd, 2H).

2. 5,6-Dihydro-1,4(4H)-thiazin-2-yl phenyl ketone

To a solution of 39.56 g (0.16M)α-acetylthio-β-dimethylaminoacrylophenone in 300 ml absolute ethanol stirring under nitrogen at 0° a solution of 8.64 g (0.16M) sodium methoxide in 230 ml ethanol is added dropwise over a period of 15 minutes. After complete addition, the dark red solution is stirred at 0 to −3° for 0.5 hours. To the solution stirring at −3° a solution of 32.79 g (0.16M) 2-bromoethylamine hydrobromide in 270 ml absolute ethanol is added dropwise over a period of 25 minutes. After complete addition the dark solution is stirred at 0° for 0.5 hours, and a solution of 8.64 g (0.16M) sodium methoxide in 230 ml absolute ethanol is added dropwise over a period of 15 minutes. The dark solution is stirred at 0° for 1 hour. The reaction mixture is allowed to warm slowly to 20° . A suspension is formed within an hour of removing the cooling bath. The reaction mixture is stirred for 16 hours at ca 20° . The suspension is cooled to 5° and acidified to pH 2 with 30 ml of a 1:1 mixture of ethanol and concentrated hydrochloric acid. The suspension is concentrated in vacuo to remove all but ca. 100 ml of ethanol. The residue is suspended in 200 ml CHCl$_3$ and the mixture is washed with water and a saturated NaCl solution. The organic layer is concentrated in vacuo to give a partially crystalline residue. This residue is triturated with a 1:1 mixture of ether and ethanol. Orange crystals are collected to give the title compound. M.P. 184°–186.5°.

The starting materials are prepared as follows:

(a) α-Acetylthioacetophenone

To a solution of 54.0 g (1.0M) sodium methoxide in 100 ml absolute ethanol stirring under nitrogen at reflux temperature 74 ml (76.1 g, 1.0M) thioacetic acid is added dropwise over a period of 0.5 hours. Upon complete addition the solution is refluxed for 15 minutes. To the yellow solution stirring under nitrogen atmosphere at reflux temperature, a solution of 199.1 g (1.0M) α-bromoacetophenone in 800 ml absolute ethanol is added rapidly dropwise over a period of 70 minutes. After complete addition, the suspension formed is refluxed for 3 hours. The reaction mixture is cooled and the precipitated NaBr is removed by vacuum filtration. The filtrate is concentrated in vacuo to give a brown oil with some solid present. This mixture is suspended in 500 ml of ether and is filtered to remove insoluble NaBr. The filtrate is stirred with activated charcoal for 0.5 hours, filtered, and concentrated in vacuo to give a red-brown oil. This oil is purified by vacuum distillation and the fraction is collected at 133°–137°/0.2–0.05 mm Hg and characterized by NMR as α-acetylthioacetophenone.

(b) α-Acetylthio-β-dimethylaminoacrylophenone 42.5 ml (0.32M) dimethylformamide dimethylacetal is added at 0° dropwise over a period of 17 minutes to 57.0 g (0.29M) α-acetylthioacetophenone stirring under nitrogen. Upon complete addition the orange solution is stirred at 0°–5° for ca. 4 hours, allowed to warm slowly to room temperature and is stirred overnight. The resulting dark solution was concentrated in vacuo to give a dark oil. The NMR spectrum confirms the presence of the enamine moiety.

3. The following compounds can be prepared by following the experimental procedure according to either one of the Examples 1 or 2:

(a) 5,6-dihydro-1-oxo-1,4(4H)-thiazin-2-yl phenyl ketone, M.P. 198°–200° ; IR: NH 3100, C=O 1575; NMR (DMSO) 7.57 (broad S, 1H), 7.33 (S, 6H), 3.72–3.35 (m, 2H), 3.25 −2.20 (m, 2H);

(b) 5,6-dihydro-1,1-dioxo-1,4(4H)-thiazin-2-yl phenyl ketone, M.P. 274°–276° ; IR (N): NH 3180 C=O 1550; NMR (DMSO) 7.62 (broad S, 1H), 7.48 (S, 6H), 3.79 (broad m, H), 3.53 (broad m, 2H);

(c) 5,6-dihydro-1,4(4H)-thiazin-2-yl 4-chlorophenyl ketone, M.P. 217°–219° ; IR(N) NH 3200, C=O 1610;

NMR (DMSO) 7.40 (s), 7.23 (d), 3.52 (m, 2H), 2.84 (m, 2H);

(d) 5,6-dihydro-1,4(4H)-thiazin-2-yl 4-bromophenyl ketone, M.P. 243°–245° ; IR(N) NH 3200, C═O 1600; NMR (DMSO) 7.68–7.20 (m), 3.53 (m, 2H), 2.85 (m, 2H);

(e) 5,6-dihydro-1,4(4H)-thiazin-2-yl 3-fluorophenyl ketone, M.P. 191°–192° ; IR(N) NH 3100, C═O 1600; NMR (DMSO) 7.67–7.13 (m, 6H), 3.53 (m, 2H), 2.84 (dd, 2H);

(f) 5,6-dihydro-1,4(4H)-thiazin-2-yl 3,4-dichlorophenyl ketone, M.P. 222°–224° ;IR(N) C═O 1605; NMR (DMSO) 7.80–7.30 (m, 5H), 3.52 (m, 2H), 2.83 (dd, 2H);

(g) 5,6-dihydro-1,4(4H)-thiazin-2-yl 2-fluorophenyl ketone, M.P. 205°–206° ; IR(N) C═O 1602; NMR (DMSO) 7.87–7.13 (m, 6H), 3.53 (m, 2H), 2.83 (dd, 2H);

(h) 5,6-dihydro-1,4(4H)-thiazin-2-yl 4-methoxyphenyl ketone, M.P. 177°–178° ; IR(N) C═O 1590; NMR (DMSO) 7.47 (s), 7.40 (s), 7.03 (s), 6.93 (s), 3.83 (s, 3H), 3.47 (m, 2H), 2.80 (dd, 2H);

(i) 5,6-dihydro-1,4(4H)-thiazin-2-yl 3-chlorophenyl ketone, M.P. 175°–176° ; IR(N) C═O 1600; NMR (DMSO) 7.42 (m, 6H), 3.52 (m, 2H), 2.83 (m, 2H);

(j) 5,6-dihydro-4-(2-piperid-1-yl-ethyl)-1,4-thiazin-2-yl 3-fluorophenyl ketone, M.P. 169°–171° ; IR(N) C═O 1560; NMR (DMSO) 7.67–7.20 (m, 5H), 3.93–2.60 (m, 12H), 1.77 (m, 6H);

(k) 5,6-dihydro-4-acetyl-1,4-thiazin-2-yl 4-fluorophenyl ketone, M.P. 152°–153° ; IR(N) C═O 1685 and 1630; NMR (DMSO) 8.00 (broad s, 1H), 7.83–7.30 (m, 5H), 4.00 (m, 2H), 3.10 (m, 2H), 2.27 (s, 3H);

(l) 5,6-dihydro-1-oxo-1,4(4H)-thiazin-2-yl 3-fluorophenyl ketone, M.P. 218°–220° ; IR(N) NH 3200, C═O 1560; NMR (DMSO) 9.13 (s, 1H), 7.80 (d), 7.47 (m), 3.77–2.87 (m, 4H);

(m) 5,6-dihydro-1,1-dioxo-1,4-(4H)-thiazin-2-yl 3-fluorophenyl ketone, M.P. 263°–266° ; IR(N) NH 3300-3200, C═O 1550; NMR (DMSO) 8.97 (broad, 1H), 7.68 (d), 7.45 (m), 3.85 (m, 2H), 3.27 (m, 2H);

(n) 5,6-dihydro-1,4(4H)-thiazin-2-yl 3-trifluoromethylphenyl ketone, M.P. 177°–179° ; IR(N) NH 3200, C═O 1600; NMR (DMSO) 8.03–7.67 (M, 5H), 7.33 (d, 1H), 3.55 (m, 2H), 2.87 (dd, 2H);

(o) 5,6-dihydro-4-methyl-1,4-thiazin-2-yl 4-fluorophenyl ketone, M.P. 122°–123°;

(p) 5,6-dihydro-1,4(4H)-thiazin-2-yl pyrid-3-yl-ketone, M.P. 197°–199° ; IR(N) NH 3250, C═O 1610; NMR (DMSO) 8.80–8.60 (M, 2H), 7.93–7.63 (m, 2H), 7.63–7.27 (m, 2H), 3.55 (m, 2H), 2.87 (m, 2H);

(q) 5,6-dihydro-1,4(4H)-thiazin-2-yl 4-carboxymethylphenyl ketone, M.P. 274°–275° ; IR(N) NH 3280, C═O 1700 and 1610; NMR (DMSO) 7.50–7.30 (m, 6H), 3.65 (s, 2H), 3.50 (m, 2H), 2.85 (m, 2H);

(r) 5,6-dihydro-1,4(4H)-thiazin-2-yl 3-carboxymethylphenyl ketone, M.P. 254°–255° ; IR(N) NH 3240 C═O 1695 and 1600; NMR (DMSO) 7.73–7.27 (m, 6H), 3.67 (s, 2H), 3.50 (m, 2H), 2.85 (m, 2H);

(s) 5-ethoxycarbonyl-5,6-dihydro-1,4(4H)-thiazin-2-yl phenyl ketone, M.P. 143°–145° ; IR(N) NH 3190, C═O 1725 and 1600; NMR (DMSO) 7.35 (s, 6H), 7.18 (d, 1H) 4.05 (m, 3H), 2.72 (m, 2H), 2.50 (m, 2H), 1.18 (t, 3H);

(t) 5-carboxymethyl-5,6-dihydro-1,4(4H)-thiazin-2-yl phenyl ketone, M.P. 251° ; IR(N) NH 3200, C═O 1700 and 1605; NMR (DMSO) 7.35 (s, 5H), 7.23 (s, 1H), 3.97 (s, 2H), 2.88–2.42 (m, 4H).

4. Preparation of 10,000 tablets each containing 100 mg of the active ingredient:

| Composition | |
|---|---|
| 5,6-dihydro-1,4(4H)-thiazin-2-yl 4-fluorophenyl ketone | 1,000.00 g |
| Lactose | 2,535.00 g |
| Corn starch | 125.00 g |
| Polyethylene glycol 6,000 | 150.00 g |
| Talcum powder | 150.00 g |
| Magnesium stearate | 40.00 g |
| Purified water | q.s |

Procedure

All the powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders which are granulated, if necessary, with an additional amount of water. The granulate is dried overnight at 35°, broken on a screen with 1.2 mm openings and compressed into tablets, using concave punches with 10.3 mm diameter, uppers bisected.

What is claimed:

1. A compound of the formula

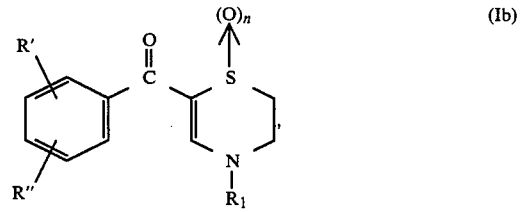

wherein $R_1$ represents hydrogen, $C_1$–$C_4$-alkanoyl, or $C_1$–$C_4$-alkyl; n is zero, one, or two; R' is hydrogen, trifluoromethyl or halogen; and R" is halogen.

2. A compound according to claim 1 of the formula Ib, wherein $R_1$ is hydrogen, n is zero, R' is hydrogen, trifluoromethyl, fluorine or chlorine, and R" is fluorine or chlorine.

3. A compound according to claim 2 of the formula Ib, wherein $R_1$ is hydrogen, n is zero, R' is hydrogen and R" is 4-fluoro being 5,6-dihydro-1,4(4H)-thiazin-2-yl 4-fluorophenyl ketone.

4. A disease-modifying antirheumatic pharmaceutical composition containing an antirheumatically effective amount of a compound of the formula Ib according to claim 1 together with a pharmaceutically acceptable adjunct or carrier.

5. A method for treating rheumatic disorders, which comprises administering to a host in need of such administration an effective disease-modifying antirheumatic amount of a compound of the formula Ib according to claim 1.

6. A disease-modifying antirheumatic pharmaceutical composition containing an antirheumatically effective amount of the compound of claim 3 together with a pharmaceutically acceptable adjunct or carrier.

7. A method of treating rheumatic disorders which comprises administering to a host in need thereof an effective disease-modifying antirheumatic amount of the compound of claim 3 or of a pharmaceutical composition comprising said compound.

* * * * *